United States Patent
Mahadevan-Jansen et al.

(10) Patent No.: US 12,383,140 B2
(45) Date of Patent: Aug. 12, 2025

(54) METHODS OF USING OPTICAL FIBER-BASED FLUORESCENCE SPECTROSCOPY FOR SURGICAL GUIDANCE AND/OR TISSUE DIAGNOSTICS AND APPLICATIONS OF SAME

(71) Applicant: VANDERBILT UNIVERSITY, Nashville, TN (US)

(72) Inventors: Anita Mahadevan-Jansen, Nashville, TN (US); Carmen C. Solorzano, Nashville, TN (US); Giju Thomas, Nashville, TN (US); Emmanuel A. Mannoh, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 420 days.

(21) Appl. No.: 17/801,862

(22) PCT Filed: Feb. 25, 2021

(86) PCT No.: PCT/US2021/019540
§ 371 (c)(1),
(2) Date: Aug. 24, 2022

(87) PCT Pub. No.: WO2021/173758
PCT Pub. Date: Sep. 2, 2021

(65) Prior Publication Data
US 2023/0165468 A1    Jun. 1, 2023

Related U.S. Application Data

(60) Provisional application No. 63/144,602, filed on Feb. 2, 2021, provisional application No. 62/981,080, filed on Feb. 25, 2020.

(51) Int. Cl.
*A61B 5/00* (2006.01)
*A61B 1/06* (2006.01)

(52) U.S. Cl.
CPC .............. *A61B 5/0059* (2013.01); *A61B 1/06* (2013.01); *A61B 5/0071* (2013.01)

(58) Field of Classification Search
CPC ... A61B 5/0071; A61B 5/0059; A61B 5/0275; A61B 2090/3933; A61B 2090/3908; A61B 2090/3904; A61B 2090/395; A61B 5/415
See application file for complete search history.

(56) References Cited

U.S. PATENT DOCUMENTS

| 6,377,841 B1 | 4/2002 | Lin et al. |
| 2017/0105623 A1† | 4/2017 | Mahadevan-Jansen |

FOREIGN PATENT DOCUMENTS

| CN | 110558938 A | 12/2019 |

OTHER PUBLICATIONS

Almquist M, Muth A. Surgical management of cytologically indeterminate thyroid nodules. Gland Surg. Aug. 2019;8(Suppl 2):S105-S111 (Year: 2019).*

(Continued)

*Primary Examiner* — Amelie R Davis
(74) *Attorney, Agent, or Firm* — troutman pepper locke; Tim Tingkang Xia, Esq.

(57) ABSTRACT

A method for intraoperatively determining a degree of parathyroid perfusion includes identifying parathyroid tissues of a living subject using autofluorescence detection with a fiber optic probe based fluorescence detection system; administering to the living subject a contrast agent with a dose; after a period of time of the administration, detecting fluorescence in an area of the parathyroid tissues with the fiber optic probe based fluorescence detection system, where the fluorescence is emitted from the contrast agent; and obtaining a detection level and/or a detection ratio for the parathyroid tissues from the detected fluorescence so as to (Continued)

determine a degree of parathyroid perfusion of each parathyroid. The method is not only unaffected by ambient light, but also has no need of images of the parathyroid tissues.

31 Claims, 5 Drawing Sheets

(56) References Cited

OTHER PUBLICATIONS

EPO, "Supplementary European Search Report for EP Application No. 21760645.8", The Hague, Germany, Dec. 8, 2023.
Giju et al., Developing a Clinical Prototype to Guide Surgeons for Intraoperative Label-Free Identification of Parathyroid Glands in Real Time, Thyroid, 2018.
F. Pattou et al., "Hypocalcemia following thyroid surgery: incidence and prediction of outcome", World Journal of Surgery, 22(7), 718-724 (1998).
G. Thomas, M. A. McWade, C. Paras, E. A. Mannoh, M. E. Sanders, L. M. White, J. T. Broome, J. E. Phay, N. Baregamian, C. C. Solórzano and A. Mahadevan-Jansen, "Developing a clinical prototype to guide surgeons for Intraoperative label-free identification of parathyroid glands in real time.", Thyroid, 28(11), 1517-1531 (2018).
R. Voelker, "Devices Help Surgeons See Parathyroid Tissue", JAMA, 320(21), 2193-2193 (2018).
J. V. Fortuny et al., "Intra-operative indocyanine green angiography of the parathyroid gland", World Journal of Surgery, 40(10), 2378-2381 (2016).
A.M. Mohs et al., "A Handheld Spectroscopic Device for In Vivo and Intraoperative Tumor Detection: Contrast Enhancement, Detection Sensitivity, and Tissue Penetration", Analytical Chemistry, 82(21), 9058-9065 (2010).
P. Jitpratoom et al., "The use of ICG enhanced fluorescence for the evaluation of parathyroid gland preservation", Gland surgery, 6(5), 579-586 (2017).
J.V. Fortuny et al., "Randomized clinical trial of intraoperative parathyroid gland angiography with indocyanine green fluorescence predicting parathyroid function after thyroid surgery: Use of indocyanine green angiography to predict postoperative parathyroid function", British Journal of Surgery, 105(4), 350-357 (2018).
E. Spartalis et al., "Intraoperative Indocyanine Green (ICG) Angiography for the Identification of the Parathyroid Glands: Current Evidence and Future Perspectives", In Vivo, 34(1), 23-32 (2020).
De Leeuw, Frederic, et al., Intraoperative Near-infrared Imaging for Parathyroid Gland Identification by Auto-fluorescence: A Feasibility Study, 8 pages, World J Surg, DOI 10.1007/s00268-016-3571-5, Published online May 24, 2016.†

\* cited by examiner
† cited by third party

METHODS OF USING OPTICAL FIBER-BASED FLUORESCENCE SPECTROSCOPY FOR SURGICAL GUIDANCE AND/OR TISSUE DIAGNOSTICS AND APPLICATIONS OF SAME

CROSS-REFERENCE TO RELATED PATENT APPLICATIONS

This PCT application claims priority to and the benefit of U.S. Provisional Patent Application Ser. Nos. 62/981,080 and 63/144,602, filed Feb. 25, 2020 and Feb. 2, 2021, respectively, which are incorporated herein by reference in their entireties.

STATEMENT AS TO RIGHTS UNDER FEDERALLY-SPONSORED RESEARCH

This invention was made with government support under Grant No. 1R01CA212147-01A1 awarded by the National Cancer Institute (NCI). The government has certain rights in the invention.

FIELD OF THE INVENTION

The invention relates generally to optical assessments of bio-objects, and more particularly, to methods of using optical fiber-based fluorescence spectroscopy for surgical guidance and/or tissue diagnostics and applications of the same.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

Parathyroid glands (PGs) regulate blood calcium levels to support heart, nervous system, kidney and bone function. They are normally about the size of a grain of rice and located within the neck beside the larger thyroid gland but can vary in location within the body and are sometimes intra-thymic or intra-thyroidal.

Due to their small size and variability in position, PGs are often difficult to distinguish from surrounding tissue and thyroid in the neck. The parathyroid visually resembles its surrounding tissue and this can extend surgical time during a parathyroidectomy. Accidental removal or damage to healthy PGs during parathyroid or thyroid surgery can result in serious complications such as hypocalcemia or hypoparathyroidism that may result from direct injury, devascularization, and/or disruption of PGs. In addition, excess secretion of parathyroid hormone as seen in primary hyperparathyroidism, disrupts normal bone and mineral metabolism, where one or more of the PGs become enlarged and hyperactive. Surgical removal of the diseased PG(s) is the only definitive treatment.

The current surgical procedure for thyroid and parathyroid surgeries involves a systematic search within the neck in which the surgeon is mainly relying on visual inspection to identify target tissues. The incidence of complications occurring due to this subjective method is directly proportional to the extent of thyroidectomy and inversely proportional to the experience of the surgeon. The disadvantages to the current method include the lengthy duration of the surgery, the exploratory nature of the surgery, and the lack of sensitive and applicable preoperative and intra-operative imaging. More importantly, it also difficult to distinguish between a well perfused PG (PGs with optimum blood supply) and a poorly perfused PG (PGs with poor or damaged blood supply). If surgeons are able to identify poorly perfused PGs on time, they can save it by autotransplantation to ensure normal parathyroid function after surgery.

Near infrared imaging with a contrast agent such as indocyanine green (ICG) is gaining prominence, where the ICG is injected and the uptake of ICG is imaged on camera. However, it is highly subjective in interpretation—varies from surgeon-to-surgeon, and lacks an objective quantitative real-time threshold to differentiate well and poorly perfused PGs. No real-time quantitative information is provided with camera systems. Depending on the camera, ICG dose ranging from 5 to 12.5 mg is used. Multiple doses need to be injected sometimes if the surgery is prolonged. In addition, the image acquisition needs to be performed in the dark, which is disruptive to the surgical workflow.

Therefore, there is a long felt need for reliable methods and systems for identifying PGs and accurately assessing the parathyroid perfusion intraoperatively.

SUMMARY OF THE INVENTION

To address the aforementioned deficiencies and inadequacies, this invention in one aspect discloses a method for intraoperatively determining a degree of parathyroid perfusion of a living subject. The method in one embodiment includes identifying parathyroid tissues of the living subject using autofluorescence detection with a fluorescence detection system; administering to the living subject a contrast agent with a dose; after a period of time of the administration, detecting fluorescence in an area of the parathyroid tissues with the fluorescence detection system, wherein the fluorescence is emitted from the contrast agent; and obtaining a detection level and/or a detection ratio for the parathyroid tissues from the detected fluorescence so as to determine a degree of parathyroid perfusion of each parathyroid.

In one embodiment, the method is unaffected by ambient light.

In one embodiment, the method is performed in real time without acquiring images of the parathyroid tissues.

In one embodiment, the method further includes, prior to said identifying the parathyroid tissues, establishing a baseline of thyroid autofluorescence intensity on the thyroid of the living subject (or muscle of the living subject, if thyroid has been removed in a previous surgery).

In one embodiment, the method further includes displaying the detection level and/or the detection ratio.

In one embodiment, the method also includes providing an auditory feedback when the detection ratio reaches a threshold value set for the parathyroid identification, and/or a threshold degree of the parathyroid perfusion.

In one embodiment, the detection level is an absolute tissue fluorescence intensity, and wherein the detection ratio is a ratio of the detected fluorescence normalized to the thyroid baseline.

In one embodiment, the threshold degree of the parathyroid perfusion depends on the dosage of the contrast agent and the period of time of the administration.

In one embodiment, the detection level and/or the detection ratio for a well vascularized parathyroid are at least 2.5 times higher than that of a poorly vascularized parathyroid.

In one embodiment, the period of time is as short as about 15 seconds. In one embodiment, the period of time is as long as about 60 minutes.

In one embodiment, the dose is as low as about 0.25 cc. In one embodiment, the dose is in a range of about 0.25-3.50 cc.

In one embodiment, the administration is systemic or by injection directly into the area of the identified parathyroid tissues.

In one embodiment, the contrast agent is indocyanine green (ICG), IRDye 800CW, or methylene blue.

In one embodiment, the fluorescence detection system comprises a laser source for emitting light having a wavelength; a fiber-optic probe for delivering the light emitted from the laser source to a target area of the living subject, and collecting fluorescence and/or autofluorescence emitted from the target area responsively; a detector for detecting intensity of the collected fluorescence and/or autofluorescence; a controller for operably activating the laser source and the detector for the fluorescence and/or autofluorescence measurements; and obtaining the detection level and/or the detection ratio from the detected fluorescence and/or autofluorescence intensity; and a display and/or a speaker, wherein the display is adapted for displaying the detection level and/or the detection ratio in real-time, and the speaker is adapted for providing an auditory feedback when the detection ratio reaches a threshold value set for the parathyroid identification, and/or a threshold degree of the parathyroid perfusion.

In one embodiment, the fiber-optic probe is a detachable and sterilizable fiber-optic probe.

In one embodiment, the wavelength is in a range of 600-900 nm. In one embodiment, the wavelength is in a near-infrared range.

In one embodiment, the fluorescence and/or autofluorescence are in a wavelength range of about 650-1000 nm.

In another aspect of the invention, the method for intraoperatively determining a degree of parathyroid perfusion of a living subject comprises identifying parathyroid tissues of the living subject using autofluorescence detection; administering to the living subject a contrast agent with a dose; after a period of time of the administration, detecting fluorescence in an area of the parathyroid tissues, wherein the fluorescence is emitted from the contrast agent; and obtaining a detection level and/or a detection ratio for the parathyroid tissues from the detected fluorescence so as to determine a degree of parathyroid perfusion of each parathyroid without acquiring images of the parathyroid tissues.

In one embodiment, the method is not affected by ambient light.

In one embodiment, the method further comprises, prior to said identifying the parathyroid tissues, establishing a baseline of thyroid autofluorescence intensity on the thyroid (or muscle autofluorescence intensity, if thyroid has been removed in a previous surgery) of the living subject.

In one embodiment, the detection level is an absolute tissue fluorescence intensity, and wherein the detection ratio is a ratio of the detected fluorescence normalized to the thyroid (or muscle, in absence of thyroid) baseline.

In one embodiment, the method further comprises displaying the detection level and/or the detection ratio.

In one embodiment, the method further comprises comprising providing an auditory feedback when the detection ratio reaches a threshold value set for the parathyroid identification, and/or a threshold degree of the parathyroid perfusion.

In one embodiment, the threshold degree of the parathyroid perfusion depends on the dosage of the contrast agent and the period of time of the administration.

In one embodiment, the detection level and/or the detection ratio for a well vascularized parathyroid are at least 2.5 times higher than that of a poorly vascularized parathyroid.

In one embodiment, the period of time is as short as about 15 seconds, or as long as about 60 minutes.

In one embodiment, the dose is in a range of about 0.25-3.50 cc.

In one embodiment, the administration is systemic or by injection directly into the area of the identified parathyroid tissues.

In one embodiment, the contrast agent is indocyanine green (ICG), RDye 800CW, or methylene blue.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein. The drawings described below are for illustration purposes only. The drawings are not intended to limit the scope of the present teachings in any way.

FIGS. 4A-4B show the NIR autofluorescence (NIRAF) for localizing/identifying PGs during thyroid procedures.

FIGS. 5A-5B show the ICG-based fluorescence for assessing PGs perfusion during thyroid procedures.

DETAILED DESCRIPTION OF THE INVENTION

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that, as used in the description herein and throughout the claims that follow, the meaning of "a", "an", and "the" includes plural reference unless the context clearly dictates otherwise. Also, it will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in this disclosure, the phrase "at least one of A, B, and C" should be construed to mean a logical (A or B or C), using a non-exclusive logical OR. As used herein, the term "and/or" includes any and all combinations of one or more of the associated listed items.

As used in this disclosure, the term "living subject" refers to a human being such as a patient, or a mammal animal such as a monkey.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Parathyroid glands (PGs) have near infrared autofluorescence (NIRAF). Currently there are very few commercial fiber optic based systems for NIR fluorescence detection. A fiber optic probe based device, PTeye (Santa Barbara, USA), is originally designed for identifying PGs by detecting NIRAF with quantitative output with more than 96% accuracy in PG identification. The PTeye was FDA cleared, and is unaffected by ambient light. A contrast agent such as indocyanine green (ICG)—a dye used for PG angiography has overlapping emission spectra with that of NIRAF from PG tissues, i.e., about 820-830 nm, and are used for enhanced fluorescence imaging as the medical tools.

Currently there are no fiber-optic probe based technology that has been applied for assessing parathyroid gland perfusion or conduct parathyroid angiography in conjunction with near infrared contrast agents such as iICG, RDye 800CW, or methylene blue. While near infrared (NIR) imaging systems have been applied for parathyroid angiography using ICG, none of these modalities can provide real-time quantitative data. In comparison, a fiber-probe based system such as the PTeye, valuable quantitative information regarding tissue perfusion can be obtained in real-time, when used in conjunction with contrast agents such as ICG, RDye 800CW, or methylene blue.

One of the objectives of this invention is to provide a novel technique that uses fiber-based fluorescence spectroscopy for angiography of parathyroid glands, and particularly a method for intraoperatively determining a degree of parathyroid perfusion of a living subject by quantifying fluorescence of a contrast agent such as iICG, RDye 800CW, or methylene blue with an optical fiber probe based fluorescence detection system. The method is unaffected by ambient light, that is, the method/procedure can be performed in real time with operation room (OR) lights remaining on during a surgical procedure. In certain embodiments, the method is performed in real time without acquiring images of the parathyroid tissues. The method is significantly different from the existing imaging method, which a dark environment is required.

Figure 1:
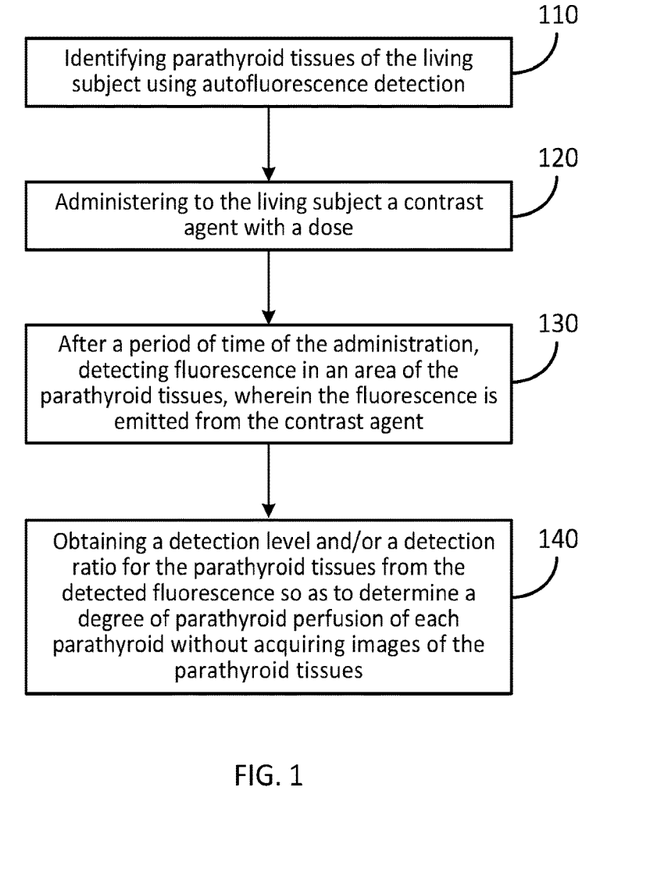
FIG. 1 shows schematically a flowchart of view of a method for intraoperatively determining a degree of parathyroid perfusion of a living subject, according to one embodiment of the invention.

Referring to FIG. 1, the method in one embodiments includes the following steps.

At step 110, parathyroid tissues of the living subject are identified using autofluorescence detection, for example, with an optical fiber probe based fluorescence detection system.

At step 120, a contrast agent with a dose is administered to the living subject. In certain embodiments, the administration is systemic or by injection directly into the area of the identified parathyroid tissues. In one embodiment, the dose is as low as about 0.25 cc. In certain embodiments, the dose is in a range of about 0.25-3.50 cc.

In certain embodiments, the contrast agent is ICG. The absorption and fluorescence spectrum of ICG is in the near infrared (NIR) region. ICG absorbs mainly between 600 nm and 900 nm and emits fluorescence between 750 nm and 950 nm. Both of the absorption and fluorescence spectra depend largely on the solvent used and the concentration. The autofluorescence of PGs at 820-825 nm is very close to fluorescence of ICG that occurs at 830-835 nm. Therefore, a fiber optic based fluorescence detection can also be an effective technique for real-time quantification to determine the degree of parathyroid perfusion. The contrast agent can also be IRDye 800CW or methylene blue.

At step 130, after a period of time of the administration, detecting fluorescence emitted from the contrast agent in an area of the parathyroid tissues is detected, for example, with the fiber optic based fluorescence detection system. In certain embodiments, the period of time is as short as about 15 seconds. In one embodiment, the period of time is as long as about 60 minutes. According to the invention, the fluorescence detection system is a fiber optic probe based fluorescence detection system and is not an imaging acquisition system, that is, the fluorescence emitted from the contrast agent is acquired by a non-imaging acquisition system.

At step 140, a detection level and/or a detection ratio for the parathyroid tissues are obtained from the detected fluorescence so as to determine a degree of parathyroid perfusion of each parathyroid.

In certain embodiments, the method further includes, prior to said identifying the parathyroid tissues, establishing a baseline of thyroid autofluorescence intensity on the thyroid of the living subject.

In certain embodiments, the detection level is an absolute tissue fluorescence intensity, and wherein the detection ratio is a ratio of the detected fluorescence normalized to the thyroid/muscle (when thyroid is absent) baseline.

In certain embodiments, the threshold degree of the parathyroid perfusion depends on the dosage of the contrast agent and the period of time of the administration.

In certain embodiments, the detection level and/or the detection ratio for a well vascularized parathyroid are at least 2.5 times higher than that of a poorly vascularized parathyroid.

In certain embodiments, the method further includes displaying the detection level and/or the detection ratio.

In certain embodiments, the method also includes providing an auditory feedback when the detection ratio reaches a threshold value set for the parathyroid identification, and/or a threshold degree of the parathyroid perfusion.

Figure 2:
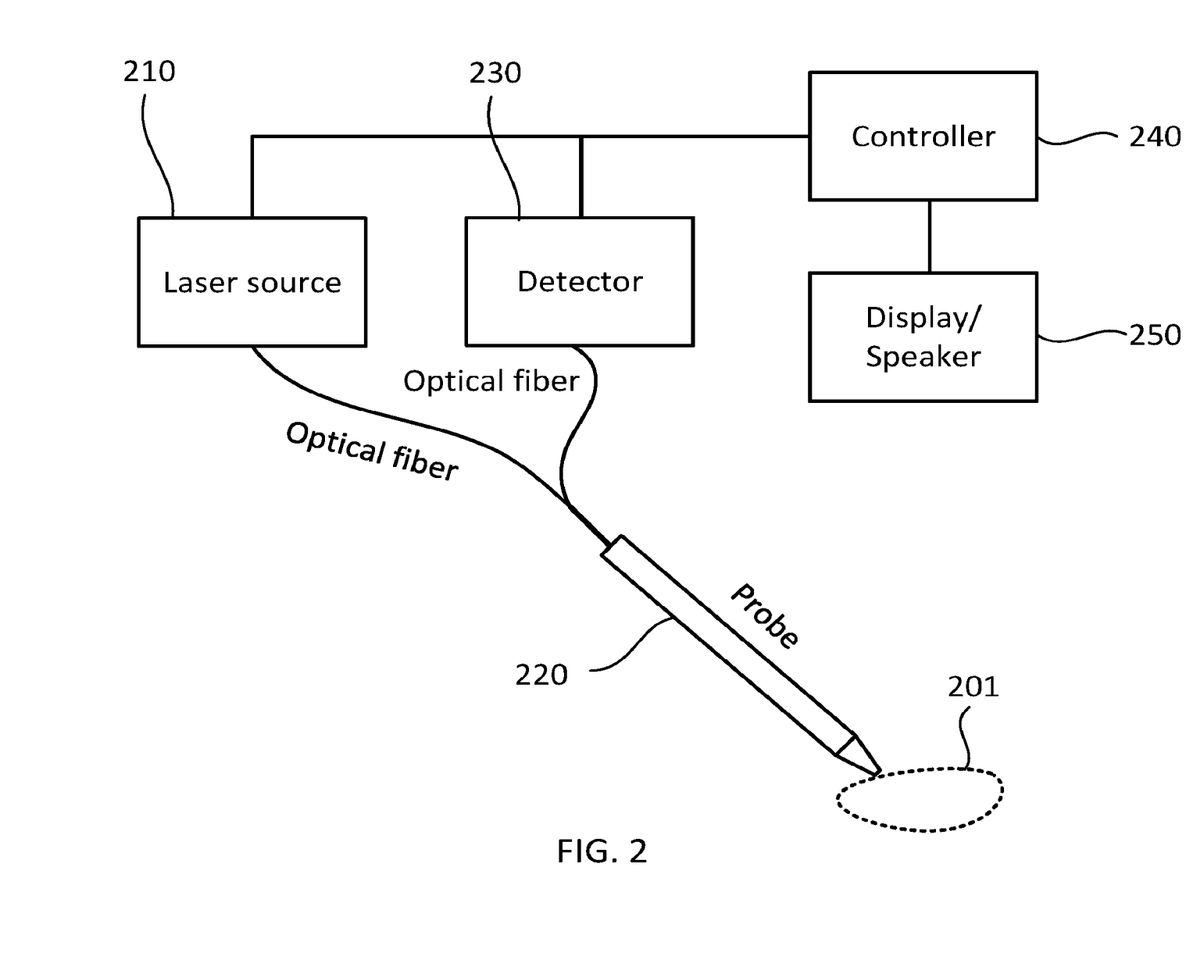
FIG. 2 shows schematically a fluorescence detection system according to one embodiment of the invention.

Referring to FIG. 2, the fiber optic probe based fluorescence detection system is schematically shown according to one embodiment of the invention. In the exemplary embodiment, the fluorescence detection system comprises a laser source 210, a fiber-optic probe 220, a detector 230, a controller 240 and a display/speaker 250.

The laser source 210 is adapted for emitting light having a wavelength in a range of about 600-900. In one embodiment, the wavelength is in the near-infrared range.

The fiber-optic probe 220 is coupled to the laser source 210 via optical fibers and adapted for delivering the light emitted from the laser source 210 to a target area 201 of the living subject, and collecting fluorescence and/or autofluorescence emitted from the target area 201 responsively. In one embodiment, the fiber-optic probe 220 is a detachable and sterilizable fiber-optic probe.

The detector 230 is coupled to the probe 220 via optical fibers and adapted for detecting intensity of the collected fluorescence and/or autofluorescence. In one embodiment, the fluorescence and/or autofluorescence are in a wavelength range of about 650-1000 nm.

The controller 240 is coupled to the laser source 210 and the detector 230 and adapted for operably activating the laser source 210 and the detector 230 for the fluorescence and/or autofluorescence measurements; and obtaining the detection level and/or the detection ratio from the detected fluorescence and/or autofluorescence intensity.

The display/speaker 250 is adapted for displaying the detection level and/or the detection ratio in real-time, and for providing an auditory feedback when the detection ratio reaches a threshold value set for the parathyroid identification, and/or a threshold degree of the parathyroid perfusion.

Figure 3:
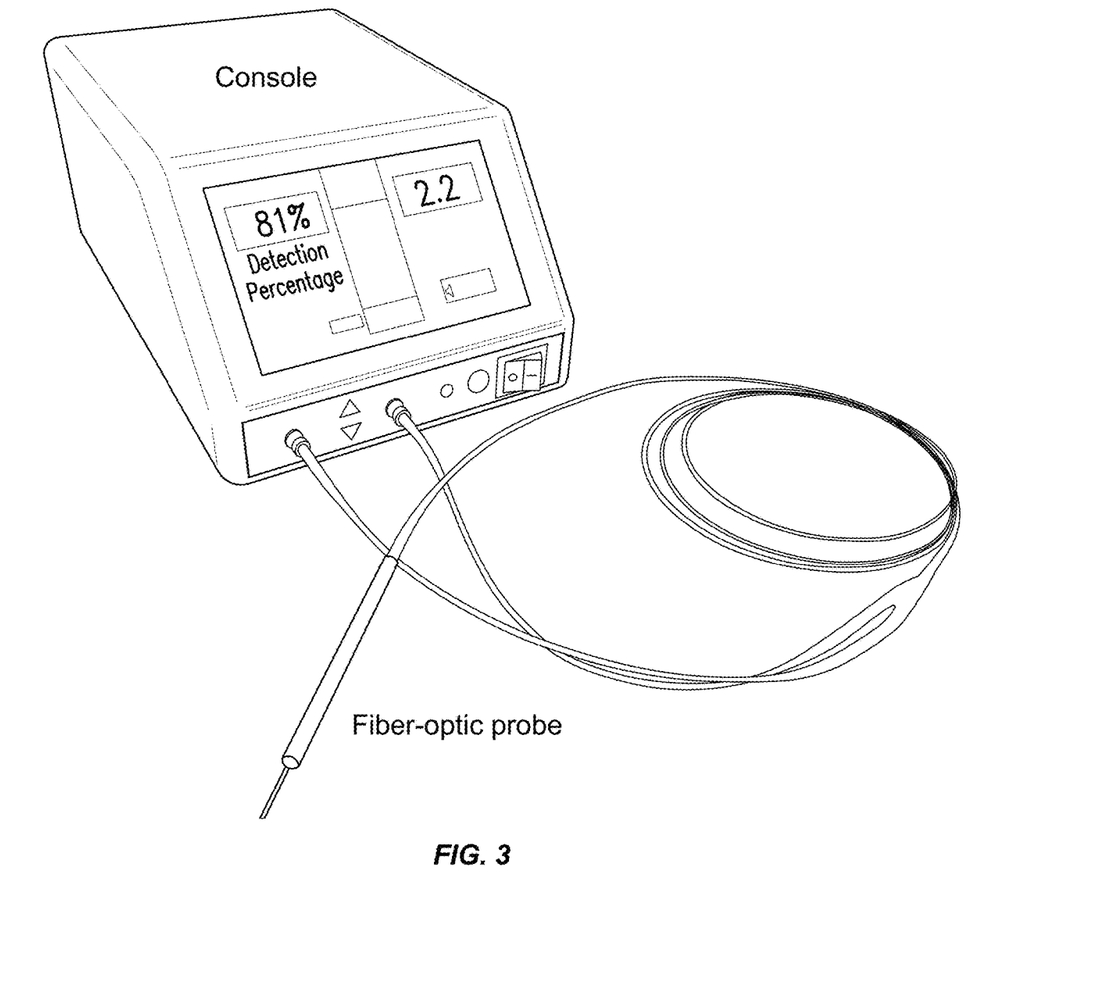
FIG. 3 shows schematically a fluorescence detection system according to one embodiment of the invention.

In one embodiment, the fluorescence detection system is a parathyroid detection system, also known as PTeye (AiBiomed, Santa Barbara, CA). It should be appreciated that other fiber optic based fluorescence detection systems can also be utilized to practice the invention. FIG. 3 shows a console and a fiber-optic probe of the PTeye. The fiber-optic probe is connected to the front of the console via two optical connectors. The PTeye also includes a foot pedal and a power cord. The foot pedal is connected to the back of the console via Lemo connector. The power supply is connected to the back of the console. The power button on the front of the console powers the system on.

The Console: The console includes, a LED display that provides information on the operation of the system including indication that the laser is on. The main components of the console includes, but are not limited to, an LED display that indicates if the laser is on; a display for visual feedback for the data collected; a speaker for auditory feedback, a photo detector; a 785 nm laser diode module—20 mW output, and two circuit boards with microprocessor, that include capability for an SD card and USB connection. The console is 5.5 inches in height by 8.5 inches in width by 13 inches in length.

The Fiber-Optic Probe: The fiber-optic probe assembly is composed of optical elements that allow for transmission of light and collection of emitted fluorescence. The components of the fiber optic probe assembly can be broken down into 3 sections; the probe tip, the probe body and the connectors. The overall length of the fiber optic probe is 2500 mm (98.4 inches).

(A) the Probe Tip Includes the Following Components:
  A transmission optical fused silica fiber that emits the 785 nm wavelength to the tissue. This full-length 600 um fused silica glass fiber has a long pass filter secured on one end with Loctite 3311 adhesive.
  A collection optical fused silica fiber that collects the desired wavelength (peak at 822 nm) from the tissue. This full-length 300 um fused silica glass fiber has a band pass filter secured on one end with Loctite 3311 adhesive.
  316 stainless steel hypo tubing used to align the band filter in the fiber tip.
  EPO-TEK 301, a medical grade epoxy that is used to secure all the optical components in the probe tip and create a seal.
  A disposable plastisol protective cap on the probe tip that is removed prior to use.
  316 stainless steel needle tube used as the probe tip to house all the optical components.
  304 stainless steel tube placed over the fiber tip to function as the probe handle.

(B) The Probe Body Includes the Following Components:
  The continuation of combined fused silica fibers extends from the probe tip to the acrylonitrile butadiene styrene (ABS) "Y" connector. After the "Y" connector, the individual fibers are split and secured to the optical connectors. Each single fiber is encased in Teflon protective tubing and covered jointly and independently in acrylate olefin heat shrink tubing.

(C) The Connectors Consist of the Following Components:
  The 300 um fiber is terminated and secured to a SMA905 connector using EPO-TEK 301 epoxy.
  The 600 um fiber is terminated and secured to a FC/PC connector using EPO-TEK 301 epoxy.

The Foot Pedal: The CE marked and UL approved foot pedal connects to the back of the console via a Lemo connector.

The External Power Supply and Power Cord: The power cord connects to the back of the console and is 8.2 feet (2.5 meters) long and rated as 125V 10 Amp. Uses a listed (UL, CSA) detachable power cord. A ferrite bead has been added to the external power supply cord. It is located 50 millimeters from the input end (console) of the cord.

The PTeye was originally designed for identifying parathyroid glands by just detecting NIR autofluorescence (NIRAF) without the use of contrast agents/dyes. The PTeye can provide detection level (tissue fluorescence intensity) and detection ratio (tissue fluorescence intensity normalized to baseline fluorescence) in the display, but cannot inform about PG perfusion/blood supply on its own. The scope of the PTeye for use in conjunction with contrast agents has not been explored or investigated yet.

To the inventors' knowledge, a fiber optic probe based fluorescence detection system such as PTeye that can provide real-time quantitative data has not been applied or utilized till date in conjunction with NIR contrast agents such as ICG, IRDye 800CW or methylene blue for blood perfusion studies, especially parathyroid angiography.

According to the invention, by using the fiber optic probe based fluorescence detection system such as the PTeye, in conjunction with contrast agents such as ICG, IRDye 800CW or methylene blue, the PTeye can now be applied for tissue perfusion studies for a real-time quantitative feedback, especially for assessment of parathyroid perfusion during head and neck surgeries. First, a surgeon establishes baseline in patient and identifies all PGs using autofluorescence detection with the PTeye (without ICG, IRDye 800CW or methylene blue). After identification of PGs, about 0.25-3.5 cc ICG (or IRDye 800CW, or methylene blue) is injected into the patient's bloodstream. After about 15-30 seconds, the PTeye probe is placed on the target PGs and the foot pedal is pressed. Detection level and Detection ratios for each PGs are recorded and compared. Detection level and detection ratios for well vascularized PGs were found to be much higher than that of poorly vascularized PGs.

The use of the PTeye in conjunction with contrast agents such as ICG, IRDye 800CW or methylene blue, for real-time assessments of the PG perfusion has at least the following advantages compared to the existing imaging methods. (i) the PTeye can detect contrast agent's fluorescence at a dose as low as 0.6 mg, compared to the imaging systems which need at least 5 mg. (ii) The PTeye can work even with the room lights remaining on during operation, and has no need to work in the dark. However, the imaging systems with ICG need to operate in the dark. (iii) The PTeye provides real-time quantitative information—the detection levels and the detection ratios. However, the imaging systems are subjective and provide no quantitative information. (iv) PGs with good blood supply have the detection level and/or the detection ratio that are at least 2.5 times higher than PGs with poor/damaged blood supply (based on the collected data till date). (v) The PTeye can detect ICG even 60 minutes after a first injection. However, for the imaging systems, ICG needs to be reinjected every 20 minutes with ICG system. (vi) The PTeye wait-time for ICG uptake is as short as about 15-30 seconds vs the camera wait-time 1-2 minutes of the imaging systems.

These and other aspects of the present invention are further described below. Without intent to limit the scope of the invention, examples according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

The PTeye is a fiber optic probe based fluorescence detection system that can detect and quantify near infrared fluorescence (>800 nm) in tissues arising from endogenous or exogenous optical contrast. With the exemplary study, we investigate the scope of the PTeye as a device that can simultaneously identify PGs in a label-free manner, while subsequently inform about PG vascularity when used in conjunction with an exogenous contrast agent such as ICG that has an emission range between about 800-860 nm.

Specifically, the exemplary studies aim at evaluation of the performance of the PTeye in real-time identification of PGs; assessments of feasibility of a fiber probe-based approach for quantifying PG perfusion with PTeye by using contrast agents such as ICG, which includes investigating the scope of PTeye in detecting ICG fluorescence—sensitivity to various ICG dosages and varying durations after ICG injection, demonstrating the feasibility of the PTeye to detect 'artificially' devascularized PGs (after gland ligation during surgery), and testing the PTeye for detecting truly 'devascularized' PGs during surgery; demonstration of the proof-of-concept with a fiber-based approach in a controlled setting—following gland ligation during parathyroidectomies, and test fiber-based approach of ICG fluorescence detection during thyroid procedures.

Materials and Methods

Patient selection: Patients (18-99 years of age) who presented at the Vanderbilt Endocrine Surgery Center for thyroidectomy or parathyroidectomy were recruited based on the eligibility as assessed by the respective surgeon during preoperative assessment. Informed written consent was obtained from all patients recruited for this study, which was approved by the Institutional Review Board of Vanderbilt University. A total of eighty-eight (88) patients were enrolled for this study—50 thyroidectomies, 32 parathyroidectomies and 6 concurrent thyroid-parathyroid surgeries. Patient data were acquired and stored in compliance with the HIPAA privacy rule.

Instrument Description: PTeye (AiBiomed, Santa Barbara, CA) comprises a console encasing a 785 nm laser source and a detector, a detachable and sterilizable fiber-optic probe, a foot pedal to activate NIR fluorescence measurements, and a display panel. The PTeye probe delivers laser light at a power of 20 mW over a spot size of about 400 The PTeye is designed to detect NIR fluorescence without interference from ambient OR lights, which has been a limitation for other standard NIR imaging systems at present. Tissue NIR fluorescence recorded with the PTeye is conveyed to the display panel and to the loudspeaker as auditory feedback. The display panel informs the surgeon on the "detection level" (absolute tissue NIR fluorescence intensity), the "detection ratio" (tissue NIR fluorescence normalized to the thyroid NIR fluorescence intensity), and the "detection percentage" (the PTeye confidence in identifying PGs [calibrated to the "detection ratio"]). The auditory feedback commences once the "detection ratio" reaches a threshold value set for PG identification.

The surgeon first confers the degree of confidence in having identified PG tissue as high, moderate, or low, based on visual inspection of the tissue in view. The surgeon then places the handheld probe of the PTeye on the tissue site and presses the foot pedal, after which tissue NIRAF intensity is displayed in real time with the OR lights remaining on. In each patient, a NIRAF baseline was first established on the thyroid so that subsequent tissue NIRAF measurements in the patient could be normalized to this thyroid baseline for obtaining the "detection ratio". The auditory feedback volume was kept inaudible and the PTeye display panel was turned away to decrease bias of the surgeon's judgment. The handheld, probe-based PTeye provides real-time guidance in identifying the parathyroid gland during surgery. When parathyroid tissue is detected, the system provides an audio signal and visual display. The system accurately identified parathyroid glands 96.1% of the time. Similar processes are also applied in in conjunction with near infrared contrast agents such as ICG for parathyroid angiography.

Evaluation of PTeye in an intraoperative setting for label-free parathyroid identification: Patients who underwent thyroidectomy, parathyroidectomy or both were recruited for this study based on the Vanderbilt Institutional Review Board approval (IRB #141648). When the surgeon visualized a potential parathyroid candidate during the procedure, the fiber-optic probe was placed on the tissue and NIRAF measurements ('detection intensity') were recorded. A detection ratio greater than about 1.2 was considered as a device positive for parathyroid. The detection ratio is a ratio of the tissue fluorescence normalized to the baseline NIRAF from thyroid tissues. System performance was cross validated with an experienced surgeon's visual confirmation for intact parathyroid and histopathology for surgically excised ones.

Evaluation of PTeye in an intraoperative setting for quantifying parathyroid perfusion using ICG: For testing the preliminary feasibility of PTeye for assessing parathyroid vascularity, patients who underwent parathyroidectomy were recruited for this aspect of the study. Prior to removal of the diseased PG, the blood supply to the gland is ligated as per routine procedure, which serves as a suitable imitation of PG devascularization for this study. After localizing the diseased PG and an adjacent healthy PG, 1 cc ICG (2.5 mg/ml) was subsequently administered into the patient's blood stream through the intravenous route. NIR fluorescence measurements were obtained from the exposed PGs before and after ICG administration.

Results

Eighty-eight patients enrolled for this study—50 thyroidectomies, 32 parathyroidectomies and 6 concurrent thyroid-parathyroid surgeries. Label-free NIRAF measurements were obtained on 237 PGs and 628 non-parathyroid sites (thyroid, muscle, fat, trachea, lymph nodes, thymic tissues), which is listed in Table 1.

TABLE 1

Patients data

| | |
|---|---|
| No. of Patients | 88 patients |
| Surgeries | 50 thyroidectomies |
| | 32 parathyroidectomies |
| | 6 combined |
| Tissue types | 237 PGs |
| | 628 Non-PG tissues |
| No. of surgeons | 2 Expert Endocrine Surgeons |

Table 2 shows the evaluation of the performance of the PTeye in real-time identification of PGs. PG identification with the PTeye is performed 'without' contrast agents.

TABLE 2

Evaluation of the performance of PTeye in real-time identification of PGs.

| | |
|---|---|
| Sensitivity (in %) | 97.5 |
| Specificity (in %) | 94.4 |
| Positive Predictive Value (in %) | 86.8 |
| Negative Predictive values (in %) | 99.0 |
| False Negative Rate (in %) | 2.5 |
| False Positive Rate (in %) | 5.6 |
| Overall accuracy (in %) | 95.3 |
| Kappa | 0.89 |

Based on these measurements, the PTeye yielded a sensitivity of 97.5% (231/237 PGs) and specificity of 94.4% (593/628 non-parathyroid regions) for an overall accuracy of 95.3%.

In addition, PTeye's potential in evaluating parathyroid vascularity by using ICG was considered in a preliminary set of 2 patients. In Patient 1, ICG administration was conducted before ligating the blood supply of the diseased PG gland, while ICG was administered only after ligating the blood supply of the diseased gland in Patient 2. The adjacent healthy gland served as control for both these patients. No notable difference in NIR fluorescence intensity was noted between the healthy PG and the ligated-diseased PG (devascularized) in Patient 1, since ICG was injected before gland ligation and hence the dye remained trapped in PG tissue due to venous stasis. In contrast, a significant difference was noted between the healthy gland and the ligated diseased gland when ICG was injected after gland ligation, with the healthy gland having NIR fluorescence intensity about 50-60 times higher than the devascularized diseased gland. Furthermore, the PTeye was able to detect NIR fluorescence in perfused PG tissues even 1 hour after ICG administration at 28.5% of the standard ICG dose (1 cc with the PTeye vs 3.5 cc with routine NIR imaging systems) typically used in perfusion studies.

Table 3 lists the sensitivity of the fiber-based fluorescence detection with respect to various ICG dosages, varying durations after ICG injection, which was tested in 5 parathyroidectomy and 3 thyroidectomy patients.

TABLE 3

Sensitivity of the fiber-based fluorescence detection with respect to ICG dosage (* represents healthy unligated PGs, and n = 14 PGs from 8 patients)

| ICG solution (2.5 mg/ml) | Detection Ratio in PG*-Pre-ICG | Detection Ratio in PG*-Post 2 min |
|---|---|---|
| 3.5 cc per injection, n = 2 PGs | 1.4-4.1 | 274.8-374.4 |
| 1 cc per injection, n = 2 PGs | 3.6-4.1 | 90.8-168.5 |
| 0.5 cc per injection, n = 1 PG | 4.5 | 19.4 |
| 0.25 cc per injection, n = 10 PGs | 2.2-5.4 | 4.5-32.8 |

It is evident that the fiber-based fluorescence detection is sensitive to NIR fluorescence from ICG dose as low as 0.25 cc (0.6 mg).

Table 4 lists the sensitivity of the fiber-based fluorescence detection respect to various ICG dosages, varying durations after ICG injection, which was tested in 3 parathyroidectomy patients.

TABLE 4

Sensitivity of using fiber-based fluorescence detection respect to time after ICG injection (*represents healthy unligated PGs, and n = 3 PGs)

| ICG solution (2.5 mg/ml) | | Pre-ICG | Post 2 min | Post 10 min | Post 20 min | Post 60 min |
|---|---|---|---|---|---|---|
| 1 cc per injection | Patient 1, PG* | 4.1 | 80.4 | 55.9 | 28.0 | Not tested |
| | Patient 1, Thyroid* | 1.1 | 45.4 | 29.7 | 13.1 | Not tested |
| | Patient 2, PG* | 3.6 | 168.5 | 84.3 | 36.3 | 18.3 |
| | Patient 2, Thyroid* | 0.7 | 205.9 | 70.3 | 49.1 | 5.2 |
| 0.5 cc per injection | Patient 3, PG* | 4.5 | 19.4 | 13.4 | Not tested | Not tested |
| | Patient 3, Thyroid* | 0.9 | 8.5 | 8.4 | Not tested | Not tested |

It is clearly shown that the fiber-based fluorescence detection is still sensitive to NIR fluorescence 20-60 minutes after a single ICG injection.

Table 5 demonstrates the feasibility of the PTeye to detect 'artificially' devascularized PGs (after gland ligation during surgery), which was tested in 4 parathyroidectomy patients. The unligated PGs had significantly higher ICG fluorescence (i.e., detection ratio) than ligated PGs.

TABLE 5 the proof-of-concept with a fiber-based approach following gland ligation during parathyroidectomies.

| | Detection Ratio in PG*-Post 2 min | |
|---|---|---|
| ICG solution (2.5 mg/ml) | Unligated PGs (healthy) | Ligated PGs (diseased) |
| 1 cc per injection, n = 6 PGs in 3 patients | 66.4-168.5 | 1.6-21.0 |
| 0.5 cc per injection, n = 3 PGs in 1 patient | 5.1-19.4 | 1.8 |

It is shown that significant difference in ICG uptake for ligated vs unligated PGs with fiber-based approach of real-time fluorescence detection. Threshold to classify vascularized and devascularized PGs would eventually depend on ICG dose administered.

Table 6 lists results of the fiber-based approach of ICG fluorescence detection during thyroid procedures.

TABLE 6 results of the fiber-based approach of ICG fluorescence detection during thyroid procedure (RSP-Right Superior PG; RIP-Right Inferior PG; LSP-Left Superior PG; LIP-Left Inferior PG, N/E-Not Surgically Explored, Total Tx-Total Thyroidectomy, and * represents PG perfusion with ICG was compared in parallel between PTeye and NIR imaging system-PDE Neo II)

| ICG solution (2.5 mg/ml), | Detection Ratios: Post 2 min ICG | | | |
|---|---|---|---|---|
| 0.25 cc per injection | RSP | RIP | LSP | LIP |
| Patient 1 (Total Tx) | 4.5 | N/E | 22.1 | N/E |
| Patient 2 (Total Tx) | 5.4 | 22.7 | 32.8 | 18.6 |
| Patient 3 (Total Tx) | 4.3 | 6.8 | 9.2 | 10.3 |
| Patient 4 (Lobectomy)* | 31.7 | 5.2 | N/E | N/E |
| Patient 5 (Lobectomy)* | 52.7 | 72.6 | N/E | N/E |

Figure 4A:
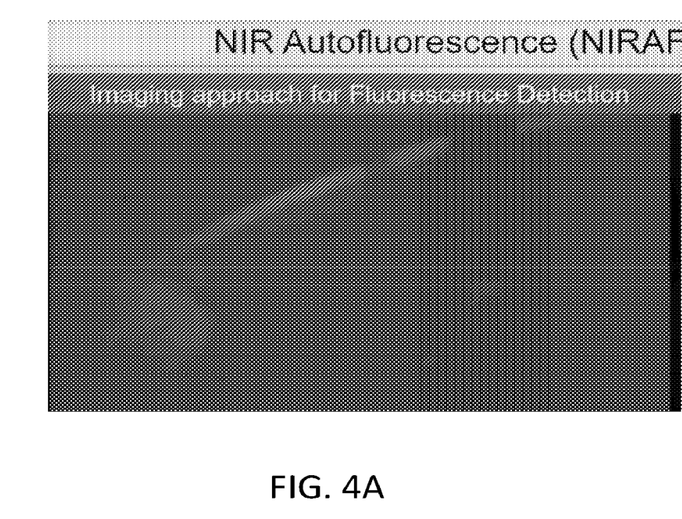
FIG. 4A: the imaging approach for fluorescence detection.
Figure 4B:
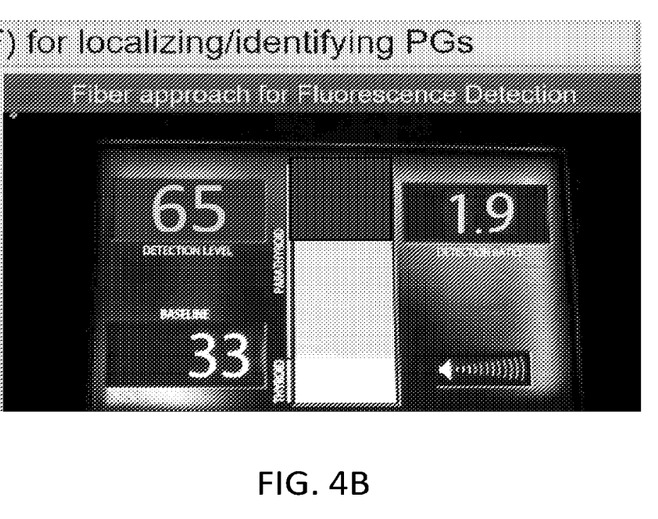
FIG. 4B: the fiber-based approach for fluorescence detection according to one embodiment of the invention.

FIGS. 4A-4B show the NIRAF for localizing/identifying PGs during thyroid procedures. FIG. 4A shows the imaging approach for fluorescence detection, while FIG. 4B shows the fiber-based approach for fluorescence detection according to one embodiment of the invention.

Figure 5A:
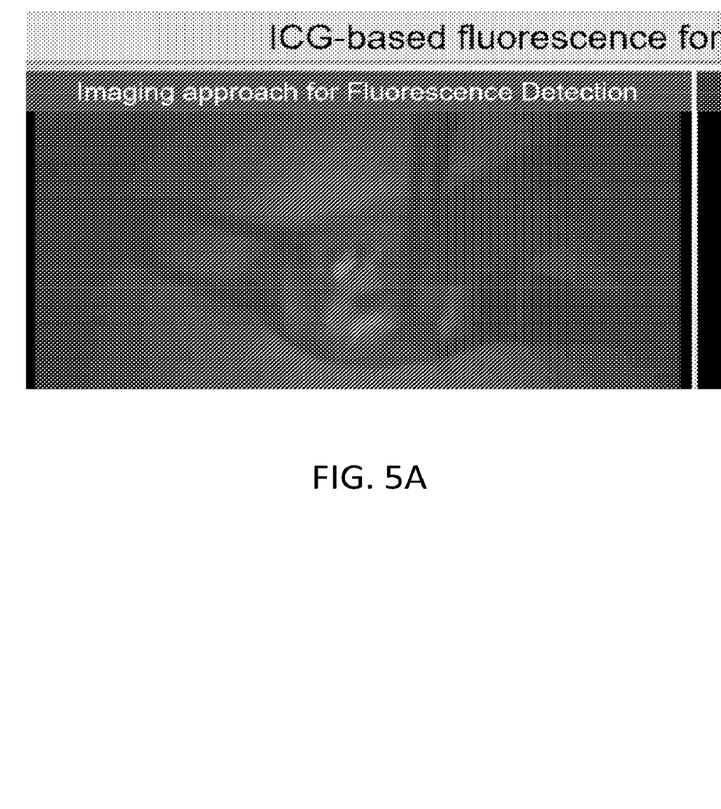
FIG. 5A: the imaging approach for fluorescence detection.
Figure 5B:
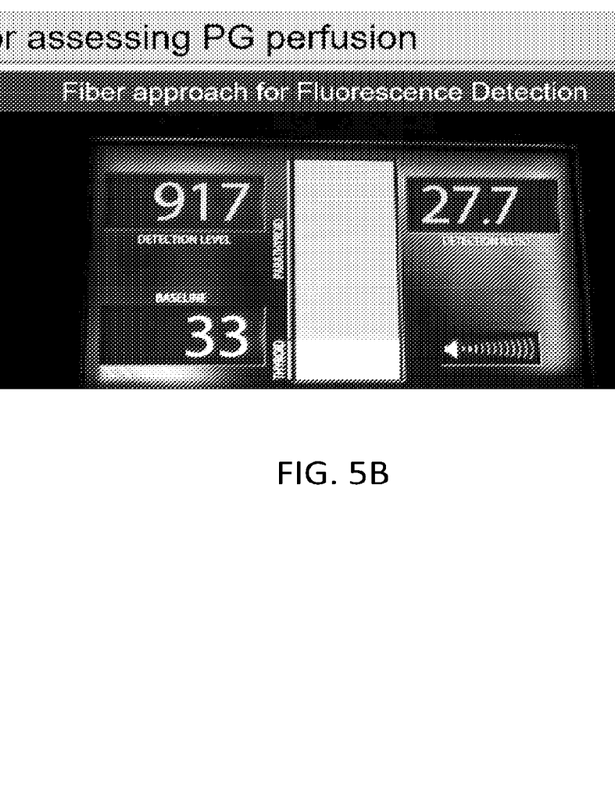
FIG. 5B: the fiber-based approach for fluorescence detection according to one embodiment of the invention.

FIGS. 5A-5B show the ICG-based fluorescence for assessing PGs perfusion during thyroid procedures. FIG. 5A shows the imaging approach for fluorescence detection, while FIG. 5B shows the fiber-based approach for fluorescence detection according to one embodiment of the invention. Both PGs 'appeared' well-vascularized apparently to the surgeon's eye.

Discussion and Summary

Our findings indicate that the PTeye demonstrate immense potential for real-time label-free parathyroid identification with 95% accuracy, by the virtue of its user-friendly display interface and ability to also function in presence of OR lights. Due to its high overall accuracy in PG, the PTeye was recently granted FDA-approval for the same application. Furthermore, we present here preliminary data that suggests that the PTeye can be valuable for sensitive assessment of PG perfusion/vascularity, in conjunction with contrast agents such as ICG.

According to the invention, the fiber probe-based approach (with the PTeye) for fluorescence detection can be a valuable intraoperative modality to identifying PGs and also concurrently quantify PG vascularity. The fiber probe-based approach also enables real-time quantitative data acquisition, while being compatible with ambient OR lights. The PTeye has a PG detection rate of 97.5% with 95.1% accuracy. Sensitive to ICG dosage as low as 0.6 mg (vs 12.5 mg required for NIR imaging). ICG was still detectable 20-60 minutes after injection. The PTeye can clearly quantify difference in ICG fluorescence between vascularized and devascularized PGs. The classification threshold would depend on ICG dosage and time of measurement after ICG injection.

Quantitative threshold to discriminate between well vascularized and poorly vascularized PGs needs to be determined, which depends on ICG dosage and time of ICG injection. Threshold of detection level and detection ratio to distinguish between PGs with good versus poor blood supply needs to be determined in larger patient dataset. Relevance to patient outcomes such as hypocalcemia needs to be determined. The need for a second baseline acquisition after ICG injection needs to be investigated.

The device software would require further optimization for eventual use in parathyroid angiography in conjunction with near infrared contrast agents such as ICG. To this effect, the scope of the PTeye has already been tested in vivo within a controlled setting such as parathyroidectomy. Difference in ICG-fluorescence between a ligated and unligated parathyroid gland could be observed and quantified in real-time with the PTeye. Further testing would be required with the PTeye in patients that undergo total thyroidectomies, where it is actually crucial to quantitatively determine parathyroid perfusion.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

[1]. American Thyroid Association. https://www.thyroid.org/media-main/about-hypothyroidism/.
[2]. F. Pattou et al., "Hypocalcemia following thyroid surgery: incidence and prediction of outcome", World Journal of Surgery, 22(7), 718-724 (1998).
[3]. G. Thomas, M. A. McWade, C. Paras, E. A. Mannoh, M. E. Sanders, L. M. White, J. T. Broome, J. E. Phay, N. Baregamian, C. C. Solórzano and A. Mahadevan-Jansen, "Developing a clinical prototype to guide surgeons for intraoperative label-free identification of parathyroid glands in real time.", Thyroid, 28(11), 1517-1531 (2018).
[4]. R. Voelker, "Devices Help Surgeons See Parathyroid Tissue", JAMA, 320(21), 2193-2193 (2018).
[5]. J. V. Fortuny et al., "Intra-operative indocyanine green angiography of the parathyroid gland", World Journal of Surgery, 40(10), 2378-2381 (2016).
[6]. A. M. Mohs et al., "A Handheld Spectroscopic Device for In Vivo and Intraoperative Tumor Detection: Contrast Enhancement, Detection Sensitivity, and Tissue Penetration", Analytical Chemistry, 82(21), 9058-9065 (2010).
[7]. P. Jitpratoom et al., "The use of ICG enhanced fluorescence for the evaluation of parathyroid gland preservation", Gland surgery, 6(5), 579-586 (2017).
[8]. J. V. Fortuny et al., "Randomized clinical trial of intraoperative parathyroid gland angiography with indocyanine green fluorescence predicting parathyroid function after thyroid surgery: Use of indocyanine green angiography to predict postoperative parathyroid function", British Journal of Surgery, 105(4), 350-357 (2018).
[9]. E. Spartalis et al., "Intraoperative Indocyanine Green (ICG) Angiography for the Identification of the Parathyroid Glands: Current Evidence and Future Perspectives", In Vivo, 34(1), 23-32 (2020).

What is claimed is:
1. A method for determining a degree of parathyroid perfusion of a living subject, comprising:
    identifying parathyroid tissues of the living subject using autofluorescence detection with a fluorescence detection system;
    administering to the living subject a contrast agent;
    detecting fluorescence in an area of the parathyroid tissues with the fluorescence detection system, wherein the fluorescence is emitted from the contrast agent;
    obtaining a detection level and/or a detection ratio for the parathyroid tissues from the detected fluorescence; and
    determining a degree of parathyroid perfusion of each parathyroid based on the detection level and/or detection ratio,
    wherein the fluorescence detection system comprises:
        a light source for emitting light having a wavelength;
        a probe for delivering the light emitted from the light source to a target area of the living subject, and collecting fluorescence and/or autofluorescence emitted from the target area responsively;
        a detector for detecting intensity of the collected fluorescence and/or autofluorescence; and
        a controller for operably activating the light source and the detector for the fluorescence and/or autofluorescence measurements, and obtaining the detection level and/or the detection ratio from the detected fluorescence and/or autofluorescence intensity.
2. The method of claim 1, being unaffected by ambient light.
3. The method of claim 1, being performed in real time without acquiring images of the parathyroid tissues.
4. The method of claim 1, further comprising, prior to said identifying the parathyroid tissues, establishing a baseline of thyroid autofluorescence intensity on the thyroid of the living subject.
5. The method of claim 4, wherein the detection level is an absolute tissue fluorescence intensity, and wherein the detection ratio is a ratio of the detected fluorescence normalized to the thyroid baseline.

6. The method of claim 1, further comprising displaying the detection level and/or the detection ratio.

7. The method of claim 1, further comprising providing an auditory feedback when the detection ratio reaches a threshold value set for the parathyroid identification, and/or a threshold degree of the parathyroid perfusion.

8. The method of claim 7, wherein the threshold degree of the parathyroid perfusion depends on the dosage of the contrast agent and the period of time of the administration.

9. The method of claim 1, wherein said parathyroid is determined as a well vascularized parathyroid, if the detection level and/or the detection ratio are at least 2.5 times higher than that of a poorly vascularized parathyroid.

10. The method of claim 1, wherein the period of time is as short as about 15 seconds.

11. The method of claim 1, wherein the period of time is as long as about 60 minutes.

12. The method of claim 1, wherein the dose is as low as about 0.25 cc.

13. The method of claim 1, wherein the dose is in a range of about 0.25-3.50 cc.

14. The method of claim 1, wherein the administration is systemic or by injection directly into the area of the identified parathyroid tissues.

15. The method of claim 1, wherein the contrast agent is indocyanine green (ICG), RDye 800CW, or methylene blue.

16. The method of claim 1, wherein the fluorescence detection system further comprises:
a display and/or a speaker, wherein the display is adapted for displaying the detection level and/or the detection ratio in real-time, and the speaker is adapted for providing an auditory feedback when the detection ratio reaches a threshold value set for the parathyroid identification, and/or a threshold degree of the parathyroid perfusion.

17. The method of claim 1, wherein the fiber-optic probe is a detachable and sterilizable fiber-optic probe.

18. The method of claim 1, wherein the wavelength is in a range of about 600-900 nm.

19. The method of claim 18, wherein the fluorescence and/or autofluorescence are in a wavelength range of about 650-1000 nm.

20. A method for intraoperatively determining a degree of parathyroid perfusion of a living subject, comprising:
identifying parathyroid tissues of the living subject using autofluorescence detection;
administering to the living subject a contrast agent with a dose;
detecting fluorescence in an area of the parathyroid tissues, wherein the fluorescence is emitted from the contrast agent; and
obtaining a detection level and/or a detection ratio for the parathyroid tissues from the detected fluorescence so as to determine a degree of parathyroid perfusion of each parathyroid without acquiring images of the parathyroid tissues,
wherein said identifying the parathyroid tissues and said detecting the fluorescence are performed by a fluorescence detection system comprising:
a laser source for emitting light having a wavelength;
a fiber-optic probe for delivering the light emitted from the laser source to a target area of the living subject, and collecting fluorescence and/or autofluorescence emitted from the target area responsively;
a detector for detecting intensity of the collected fluorescence and/or autofluorescence; and
a controller for operably activating the laser source and the detector for the fluorescence and/or autofluorescence measurements; and obtaining the detection level and/or the detection ratio from the detected fluorescence and/or autofluorescence intensity.

21. The method of claim 20, being unaffected by ambient light.

22. The method of claim 21, further comprising, prior to said identifying the parathyroid tissues, establishing a baseline of thyroid autofluorescence intensity on the thyroid of the living subject.

23. The method of claim 22, wherein the detection level is an absolute tissue fluorescence intensity, and wherein the detection ratio is a ratio of the detected fluorescence normalized to the thyroid baseline.

24. The method of claim 20, further comprising displaying the detection level and/or the detection ratio.

25. The method of claim 20, further comprising providing an auditory feedback when the detection ratio reaches a threshold value set for the parathyroid identification, and/or a threshold degree of the parathyroid perfusion.

26. The method of claim 25, wherein the threshold degree of the parathyroid perfusion depends on the dosage of the contrast agent and the period of time of the administration.

27. The method of claim 20, wherein said parathyroid is determined as a well vascularized parathyroid, if the detection level and/or the detection ratio are at least 2.5 times higher than that of a poorly vascularized parathyroid.

28. The method of claim 20, wherein the period of time is as short as about 15 seconds, or as long as about 60 minutes.

29. The method of claim 20, wherein the dose is in a range of about 0.25-3.50 cc.

30. The method of claim 20, wherein the administration is systemic or by injection directly into the area of the identified parathyroid tissues.

31. The method of claim 20, wherein the contrast agent is indocyanine green (ICG), RDye 800CW, or methylene blue.

* * * * *

UNITED STATES PATENT AND TRADEMARK OFFICE
CERTIFICATE OF CORRECTION

PATENT NO. : 12,383,140 B2
APPLICATION NO. : 17/801862
DATED : August 12, 2025
INVENTOR(S) : Anita Mahadevan-Jansen et al.

It is certified that error appears in the above-identified patent and that said Letters Patent is hereby corrected as shown below:

In the Specification

Column 1, Lines 16-22: reading:
"This invention was made with government support under Grant No. 1R01CA212147-01A1 awarded by the National Cancer Institute (NCI). The government has certain rights in the invention."

Should read as follows:
-- This invention was made with government support under CA212147 awarded by the National Institutes of Health. The government has certain rights in the invention. --

Signed and Sealed this
Twenty-third Day of September, 2025

John A. Squires
*Director of the United States Patent and Trademark Office*